United States Patent
Blinn et al.

(10) Patent No.: US 7,105,199 B2
(45) Date of Patent: Sep. 12, 2006

(54) METHODS OF ADHERING DRUGS TO THE SURFACE OF MEDICAL DEVICES THROUGH ION BEAM SURFACE MODIFICATION

(75) Inventors: Stephen M. Blinn, North Reading, MA (US); Barry M. Zide, Medway, MA (US); Vincent DiFilippo, North Chelmsford, MA (US); Sean Kirkpatrick, Littleton, MA (US)

(73) Assignee: Exogenesis Corporation, Wellesley Hills, MA (US)

( * ) Notice: Subject to any disclaimer, the term of this patent is extended or adjusted under 35 U.S.C. 154(b) by 277 days.

(21) Appl. No.: 10/144,919

(22) Filed: May 13, 2002

(65) Prior Publication Data

US 2002/0188324 A1 Dec. 12, 2002

Related U.S. Application Data

(60) Provisional application No. 60/317,652, filed on Sep. 6, 2001, provisional application No. 60/290,389, filed on May 11, 2001.

(51) Int. Cl.
*B05D 3/00* (2006.01)
*C23C 14/00* (2006.01)
(52) U.S. Cl. .................... 427/2.24; 427/2.25; 427/523; 427/534
(58) Field of Classification Search ............. 427/2.24, 427/2.25, 523, 533, 534
See application file for complete search history.

(56) References Cited

U.S. PATENT DOCUMENTS

| 5,123,924 | A | 6/1992 | Sioshansi et al. |
| 5,459,326 | A | 10/1995 | Yamada |
| 5,814,194 | A | 9/1998 | Deguchi et al. |
| 6,331,227 | B1 | 12/2001 | Dykstra et al. |
| 6,491,800 | B1 * | 12/2002 | Kirkpatrick et al. ... 204/192.34 |
| 6,635,082 | B1 * | 10/2003 | Hossainy et al. .......... 623/1.15 |
| 6,641,607 | B1 * | 11/2003 | Hossainy et al. .......... 623/1.15 |
| 6,676,989 | B1 * | 1/2004 | Kirkpatrick et al. ....... 427/2.28 |
| 6,716,444 | B1 * | 4/2004 | Castro et al. ............... 424/422 |
| 6,764,505 | B1 * | 7/2004 | Hossainy et al. .......... 623/1.15 |
| 6,863,786 | B1 * | 3/2005 | Blinn et al. ............ 204/192.34 |
| 2002/0017454 | A1 * | 2/2002 | Kirkpatrick ............ 204/192.34 |
| 2002/0139961 | A1 * | 10/2002 | Kinoshita et al. ........... 252/500 |
| 2003/0009233 | A1 * | 1/2003 | Blinn et al. ............. 623/22.11 |
| 2005/0025804 | A1 * | 2/2005 | Heller ........................ 424/423 |

FOREIGN PATENT DOCUMENTS

JP 10066721 A 3/1998

* cited by examiner

*Primary Examiner*—Bret Chen
(74) *Attorney, Agent, or Firm*—Jerry Cohen; David W. Gomes; Burns & Levinson LLP

(57) ABSTRACT

Methods of implanting, applying, or adhering various drug molecules directly into or onto the surface of medical devices through gas cluster ion beam (GCIB) and/or monomer ion beam surface modification of the medical devices before or after depositing the various drug molecules onto the medical devices.

16 Claims, 7 Drawing Sheets

METHODS OF ADHERING DRUGS TO THE SURFACE OF MEDICAL DEVICES THROUGH ION BEAM SURFACE MODIFICATION

CROSS REFERENCE TO RELATED APPLICATIONS

This application claims priority of U.S. provisional application Ser. No. 60/290,389 entitled "Method and System for Improving the Effectiveness of Medical Devices by Applying/Adhering Drugs to their Surface in Combination with the Application of Ion Beam Technology", filed May 11, 2001, and U.S. provisional application Ser. No. 60/317,652 entitled "Method and System for Improving the Effectiveness of Medical Devices by Applying/Adhering Drugs to their Surface in Combination with the Application of Ion Beam Technology", filed Sep. 6, 2001, both applications being incorporated herein by reference.

FIELD OF THE INVENTION

This invention relates generally to medical devices implantable in a mammal, such as coronary stents and to a method and system for applying and adhering drugs to the surface of medical devices using gas cluster ion beam technology and/or monomer ion beam technology. The invention can also be used with implantable prostheses.

BACKGROUND OF THE INVENTION

A coronary stent is an implantable medical device that is used in combination with balloon angioplasty. Balloon angioplasty is a procedure used to treat coronary atherosclerosis. Balloon angioplasty compresses built-up plaque against the walls of the blocked artery by the inflation of a balloon at the tip of a catheter inserted into the artery during the angioplasty procedure. Unfortunately, the body's response to this procedure often includes thrombosis or blood clotting and the formation of scar tissue or other trauma-induced tissue reactions at the treatment site. Statistics show that restenosis or renarrowing of the artery by scar tissue after balloon angioplasty occurs in up to 35 percent of the treated patients within only six months after these procedures, leading to severe complications in many patients.

To reduce restenosis, cardiologists are now often placing a small metal tubular devices of various forms, such as wire mesh or expandable metal, called a coronary stent at the site of blockage during balloon angioplasty. The goal is to have the stent act as a scaffold to keep the coronary artery open after the removal of the balloon.

However, there are also serious complications associated with the use of coronary stents. Coronary restenotic complications associated with stents occur in 16 to 22 percent of all cases within six months after insertion of the stent and are believed to be caused by many factors acting alone or in combination. These complications could be reduced by several type of drugs introduced locally at the site of stent implantation. Because of the substantial financial costs associated with treating the complications of restenosis, such as catheterization, restenting, intensive care, etc., a reduction in restenosis rates would save money and reduce patient suffering.

Numerous studies suggest that the current popular designs of coronary stents are functionally equivalent and suffer a 16 to 22 percent rate of restenosis. Although the use of coronary stents is growing, the benefits of their use remain controversial in certain clinical situations or indications due to their potential complications. It is widely held that during the process of expanding the stent, damage occurs to the endothelial lining of the blood vessel triggering a healing response that re-occludes the artery. To help combat that phenomenon, drug-coated stents are being introduced to the market to help control the abnormal cell growth associated with this healing response. These drugs are typically mixed with a liquid polymer and applied to the stent surface. When implanted, the drug elutes out of the polymer in time, releasing the medicine into the surrounding tissue. There remain a number of problems associated with this technology. Because the stent is expanded at the diseased site the polymeric material has a tendency to crack and sometimes delaminate from the stent surface. These polymer flakes can travel throughout the cardio-vascular system and cause significant damage. There is some evidence to suggest that the polymers themselves cause a toxic reaction in the body. Additionally, because of the thickness of the coating necessary to carry the required amount of medicine, the stents can become somewhat rigid making expansion difficult. In other prior art stents, the wire mesh of the stent itself is impregnated with one or more drugs through processes such as high pressure loading, spraying, and dipping. However, loading, spraying and dipping do not satisfactorily adhere the drug to the stent surface and therefore, in many instances, do not yield the optimal dosage of the drugs delivered to the surrounding tissue.

It is therefore an object of this invention to provide a means of applying and adhering drugs to medical devices using gas cluster ion beam technology and/or monomer ion beam technology.

It is a further object of this invention to apply drugs to medical stents by gas cluster ion beams and/or monomer ion beams to decrease the complication of restenosis and thrombosis.

SUMMARY OF THE INVENTION

The objects set forth above as well as further and other objects and advantages of the present invention are achieved by the invention described hereinbelow.

The present invention is directed to the use of gas cluster ion-beam (GCIB) surface modification and/or monomer ion beam surface modification to implant, apply, or adhere various drug molecules directly into or onto the surface of a stent or other medical device thereby eliminating the need for a polymer or any other binding agent. This will prevent the problem of toxicity and the damage caused by transportation of delaminated polymeric material throughout the body. Further, unlike other prior art stents that load the stent material itself, the optimal dosage of the drug may be applied or adhered.

The application of the drug is achieved through the use of GCIB technology and/or monomer ion beam technology. The application of the drug is accomplished by several methods:

First a stent is processed using a GCIB and/or a monomer ion beam which will remove any contaminants and oxide layers from the surface rendering the surface electrically active and creating dangling bonds. The desired drug will then be introduced to the active surface and will bond with the dangling bonds.

A second method is to coat the stent surface with medicine in liquid form, impact the surface with energetic ion beam clusters and/or monomer ions implanting the drug molecules sub-surface in the form of a mechanical bond.

The third method is to electrostatically coat the stent surface with medicine in powder form and implant the drug molecules in the same manner described in the second method.

The application of drugs via gas cluster ion beam (GCIB) surface modification and/or monomer ion beam surface modification such as described above will reduce complications, lead to genuine cost savings and an improvement in patient quality of life, and overcome prior problems of thrombosis and restenosis.

For a better understanding of the present invention, together with other and further objects thereof, reference is made to the accompanying drawings and detailed description.

DETAILED DESCRIPTION OF THE PREFERRED METHODS AND EMBODIMENTS

Figure 1:
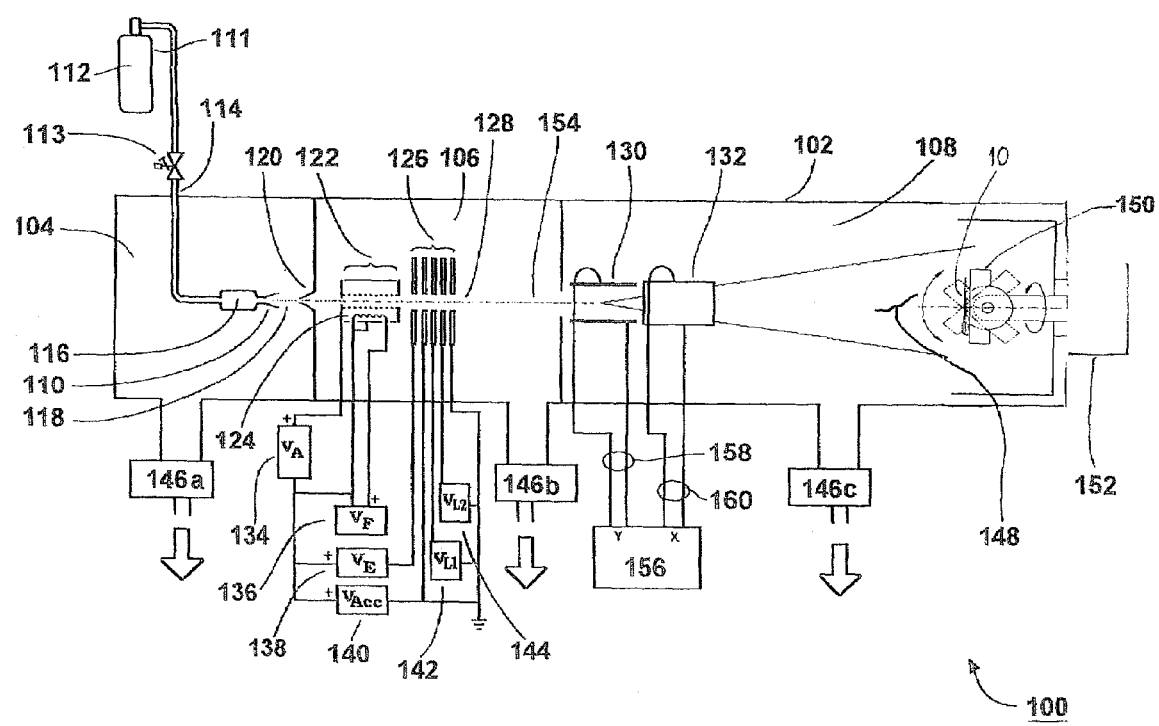
FIG. 1 is a schematic view of a gas cluster ion beam processing system of the present invention.

Beams of energetic ions, electrically charged atoms or molecules accelerated through high voltages under vacuum, are widely utilized to form semiconductor device junctions, to smooth surfaces by sputtering, and to enhance the properties of thin films. In the present invention, these same beams of energetic ions are utilized for the applying and adhering drugs to a surface of a medical device, such as a coronary stent.

In the preferred embodiment of the present invention, gas cluster ion beam (GCIB) processing is utilized. Gas cluster ions are formed from large numbers of weakly bound atoms or molecules sharing common electrical charges and accelerated together through high voltages to have high total energies. Cluster ions disintegrate upon impact and the total energy of the cluster is shared among the constituent atoms. Because of this energy sharing, the atoms are individually much less energetic than the case of conventional ions or ions not clustered together and, as a result, the atoms penetrate to much shorter depths. Surface sputtering effects are orders of magnitude stronger than corresponding effects produced by conventional ions, thereby making important microscale surface effects possible that are not possible in any other way.

The concept of GCIB processing has only emerged over the past decade. Using a GCIB for dry etching, cleaning, and smoothing of materials is known in the art and has been described, for example, by Deguchi, et al. in U.S. Pat. No. 5,814,194, "Substrate Surface Treatment Method", 1998. Because ionized clusters containing on the order of thousands of gas atoms or molecules may be formed and accelerated to modest energies on the order of a few thousands of electron volts, individual atoms or molecules in the clusters may each only have an average energy on the order of a few electron volts. It is known from the teachings of Yamada in, for example, U.S. Pat. No. 5,459,326, that such individual atoms are not energetic enough to significantly penetrate a surface to cause the residual sub-surface damage typically associated with plasma polishing. Nevertheless, the clusters themselves are sufficiently energetic (some thousands of electron volts) to effectively etch, smooth, or clean hard surfaces.

Because the energies of individual atoms within a gas cluster ion are very small, typically a few eV, the atoms penetrate through only a few atomic layers, at most, of a target surface during impact. This shallow penetration of the impacting atoms means all of the energy carried by the entire cluster ion is consequently dissipated in an extremely small volume in the top surface layer during a period on the order of 10–12 seconds (i.e. one picosecond). This is different from the case of ion implantation which is normally done with conventional monomer ions and where the intent is to penetrate into the material, sometimes penetrating several thousand angstroms, to produce changes in the surface properties of the material. Because of the high total energy of the cluster ion and extremely small interaction volume, the deposited energy density at the impact site is far greater than in the case of bombardment by conventional monomer ions.

Reference is now made to FIG. 1 of the drawings which shows the gas cluster ion beam (GCIB) processor 100 of this invention utilized for applying or adhering drugs to the surface of a coronary stent 10. Although not limited to the specific components described herein, the processor 100 is made up of a vacuum vessel 102 which is divided into three communicating chambers, a source chamber 104, an ionization/acceleration chamber 106, and a processing chamber 108 which includes therein a uniquely designed workpiece holder 150 capable of positioning the medical device for uniform GCIB bombardment and drug application by a gas cluster ion beam.

During the drug application method of this invention, the three chambers are evacuated to suitable operating pressures by vacuum pumping systems 146a, 146b, and 146c, respectively. A condensable source gas 112 (for example argon or N2) stored in a cylinder 111 is admitted under pressure through gas metering valve 113 and gas feed tube 114 into stagnation chamber 116 and is ejected into the substantially lower pressure vacuum through a properly shaped nozzle 110, resulting in a supersonic gas jet 118. Cooling, which results from the expansion in the jet, causes a portion of the gas jet 118 to condense into clusters, each consisting of from several to several thousand weakly bound atoms or molecules. A gas skimmer aperture 120 partially separates the gas molecules that have not condensed into a cluster jet from the cluster jet so as to minimize pressure in the downstream regions where such higher pressures would be detrimental (e.g., ionizer 122, high voltage electrodes 126, and process chamber 108). Suitable condensable source gases 112 include, but are not necessarily limited to argon, nitrogen, carbon dioxide, oxygen.

After the supersonic gas jet 118 containing gas clusters has been formed, the clusters are ionized in an ionizer 122. The ionizer 122 is typically an electron impact ionizer that produces thermoelectrons from one or more incandescent filaments 124 and accelerates and directs the electrons causing them to collide with the gas clusters in the gas jet 118, where the jet passes through the ionizer 122. The electron impact ejects electrons from the clusters, causing a portion the clusters to become positively ionized. A set of suitably biased high voltage electrodes 126 extracts the cluster ions from the ionizer 122, forming a beam, then accelerates the cluster ions to a desired energy (typically from 1 keV to several tens of keV) and focuses them to form a GCIB 128 having an initial trajectory 154. Filament power supply 136 provides voltage $V_F$ to heat the ionizer filament 124. Anode power supply 134 provides voltage $V_A$ to accelerate thermoelectrons emitted from filament 124 to cause them to bombard the cluster containing gas jet 118 to produce ions. Extraction power supply 138 provides voltage $V_E$ to bias a high voltage electrode to extract ions from the ionizing region of ionizer 122 and to form a GCIB 128. Accelerator power supply 140 provides voltage $V_{Acc}$ to bias a high voltage electrode with respect to the ionizer 122 so as to result in a total GCIB acceleration energy equal to $V_{Acc}$ electron volts (eV). One or more lens power supplies (142 and 144, for example) may be provided to bias high voltage electrodes with potentials ($V_{L1}$ and $V_{L2}$ for example) to focus the GCIB 128.

A medical device 10, such as a coronary stent, to be processed by the GCIB processor 100 is held on a workpiece holder 150, and disposed in the path of the GCIB 128 for irradiation. The present invention may be utilized with medical devices composed of a variety of materials, such as metal, polyethylene, ceramic, or combinations thereof. In order for the stent to be uniformly processed using GCIB, the workpiece holder 150 is designed in a manner set forth below to manipulate the stent 10 in a specific way.

Figure 2:
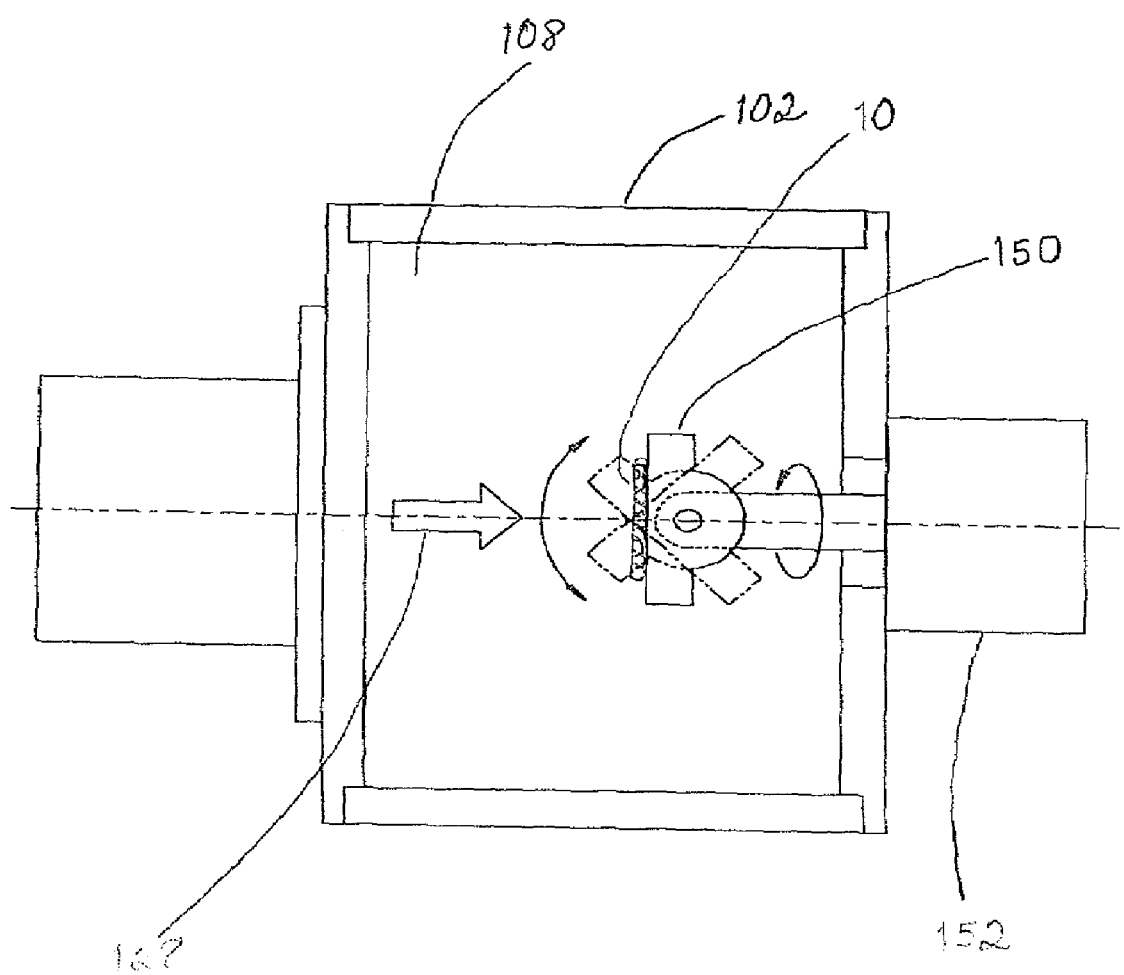
FIG. 2 is an exploded view of a portion of the gas cluster ion beam processing system showing the workpiece holder.

Referring now to FIG. 2 of the drawings, stent surfaces that are non-planar must remain oriented within a specific angle tolerance with respect to the normal beam incidence to obtain paramount effect to the stent surfaces utilizing GCIB. This requires a fixture or workpiece holder 150 with the ability to be fully articulated to orient all non-planar surfaces of stent 10 to be modified within that specific angle tolerance at a constant exposure level for process optimization and uniformity. Any stent 10 containing surfaces that would be exposed to the process beam at angles of greater than +/−15 degrees from normal incidence may require manipulation. More specifically, when applying GCIB to a coronary stent 10, the workpiece holder 150 is rotated and articulated by a mechanism 152 located at the end of the GCIB processor 100. The articulation/rotation mechanism 152 preferably permits 360 degrees of device rotation about longitudinal axis 154 and sufficient device articulation about an axis 156 perpendicular to axis 154 to maintain the stent's surface to within +/−15 degrees from normal beam incidence.

Under certain conditions, depending upon the size of the coronary stent 10, a scanning system may be desirable to produce uniform smoothness. Although not necessary for GCIB processing, two pairs of orthogonally oriented electrostatic scan plates 130 and 132 may be utilized to produce a raster or other scanning pattern over an extended processing area. When such beam scanning is performed, a scan generator 156 provides X-axis and Y-axis scanning signal voltages to the pairs of scan plates 130 and 132 through lead pairs 158 and 160 respectively. The scanning signal voltages are commonly triangular waves of different frequencies that cause the GCIB 128 to be converted into a scanned GCIB 148, which scans the entire surface of the stent 10.

When beam scanning over an extended region is not desired, processing is generally confined to a region that is defined by the diameter of the beam. The diameter of the beam at the stent's surface can be set by selecting the voltages ($V_{L1}$ and/or $V_{L2}$) of one or more lens power supplies (142 and 144 shown for example) to provide the desired beam diameter at the workpiece.

In one embodiment of the present invention, the surface of the medical device is irradiated with the gas cluster ion beam prior to the deposition of any drug on the surface thereof. This will remove any contaminants and oxide layers from the stent surface rendering the surface electrically active and capable of attracting and bonding drug molecules that are then introduced to the surface. One or more types of drugs are deposited upon surface through vapor phase deposition or by introducing a liquid form of the drug onto the surface. In some instances, the liquid form of the drug is in solution with a volatile solvent thereby requiring the solvent to be evaporated. As the formed mechanical bonds are broken over time, the drug is slowly released to the site of stent implantation.

Studies have suggested that a wide variety of drugs may be useful at the site of contact between the medical device and the in vivo environment. For example, drugs such as anti-coagulants, anti-prolifics, antibiotics, immune-supressing agents, vasodilators, anti-thrombotic substances, anti-platelet substances, and cholesterol reducing agents may reduce instances of restenosis when diffused into the blood vessel wall after insertion of the stent.

In yet another embodiment of the present invention, GCIB processing is utilized to impact the surface with energetic clusters thus implanting and forming a mechanical bond to the drug molecules of the medicine that had been applied in liquid form to coat the stent surface; or to implant the drug molecules of the electrostatically coated medicine in powder form to the stent surface in the same manner described above. The impact energy of the gas clusters results in a portion of the deposited drug molecules to form a carbon matrix at the surface. As the carbon matrix is formed, the remaining drug molecules become embedded within the interstices of the matrix. Over time, these drug molecules diffuse through the matrix and are released at the contact site between the stent and the blood vessel wall thereby continuously providing medication to the site.

Figure 3:
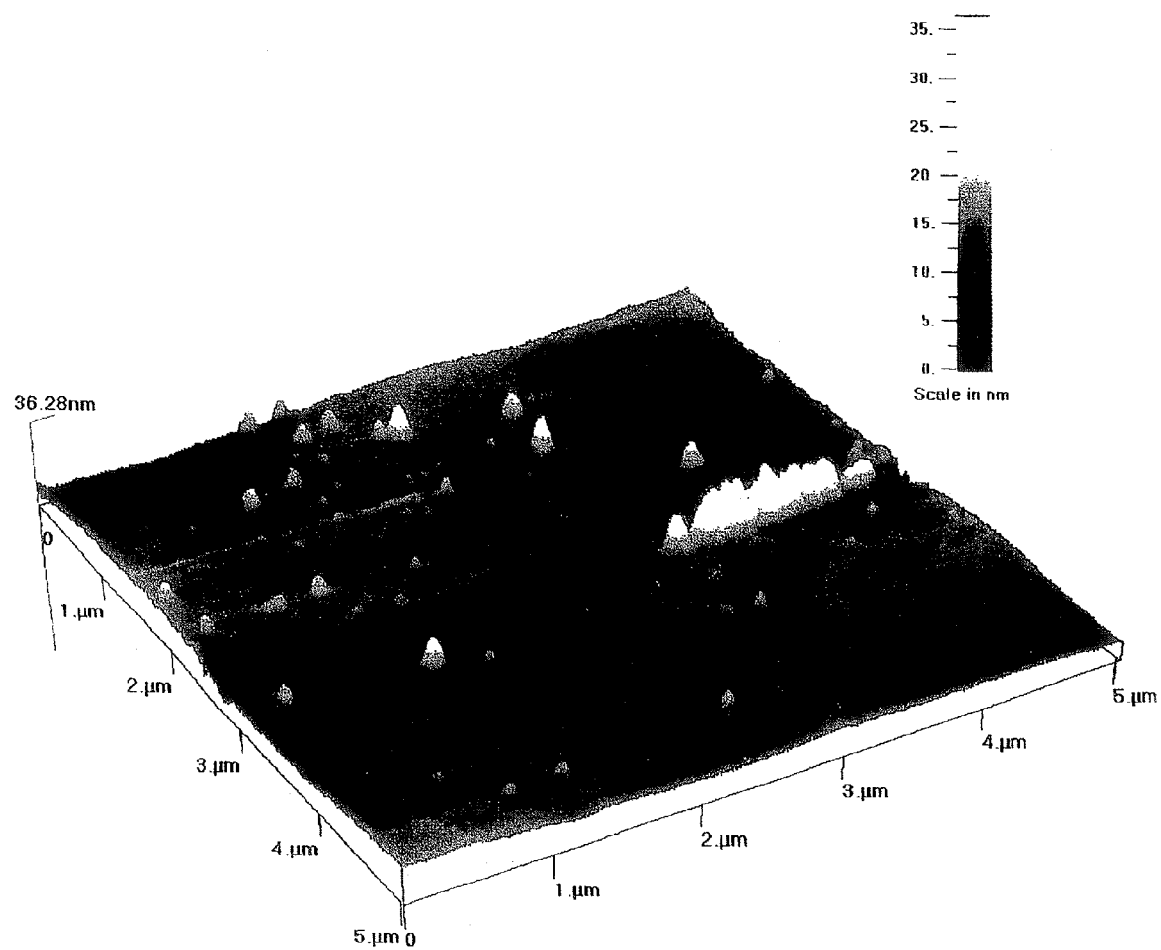
FIG. 3 is an atomic force microscope image showing the surface of a coronary stent before GCIB processing.
Figure 4:
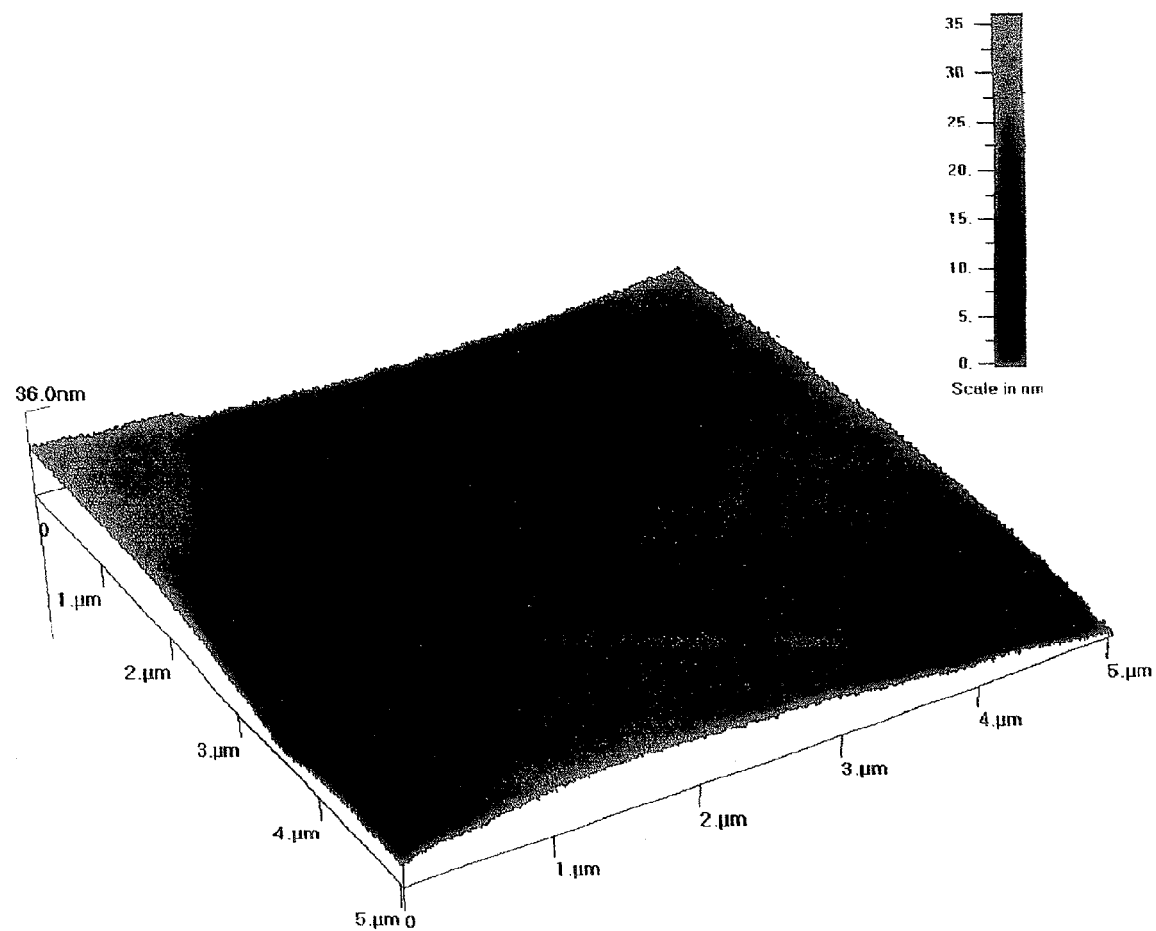
FIG. 4 is an atomic force microscope image showing the surface of a coronary stent after GCIB processing.

As the atomic force microscope (AFM) images shown in FIGS. 3 and 4 demonstrate, it is possible to dramatically affect the surface on stents utilizing one embodiment of the present invention. FIG. 3 shows a stent before GCIB treatment with gross surface micro-roughness on a strut edge. The surface roughness measured an $R_a$ of 113 angstroms and an $R_{RMS}$ of 148 angstroms. These irregularities highlight the surface condition at the cellular level where thrombosis begins. FIG. 4 shows a stent after GCIB processing where the surface micro-roughness has been eliminated without any measurable physical or structural change to the integrity of the stent itself. The post-GCIB surface roughness measured an $R_a$ of 19 angstroms and an $R_{RMS}$ of 25 angstroms. In this manner, GCIB processing also provides the added benefit of smoothing the surface of the medical device while applying/adhering the drug to the surface. Non-smooth surfaces may snare fibrinogen, platelets, and other matter further promoting stenosis to occur.

Figure 5:
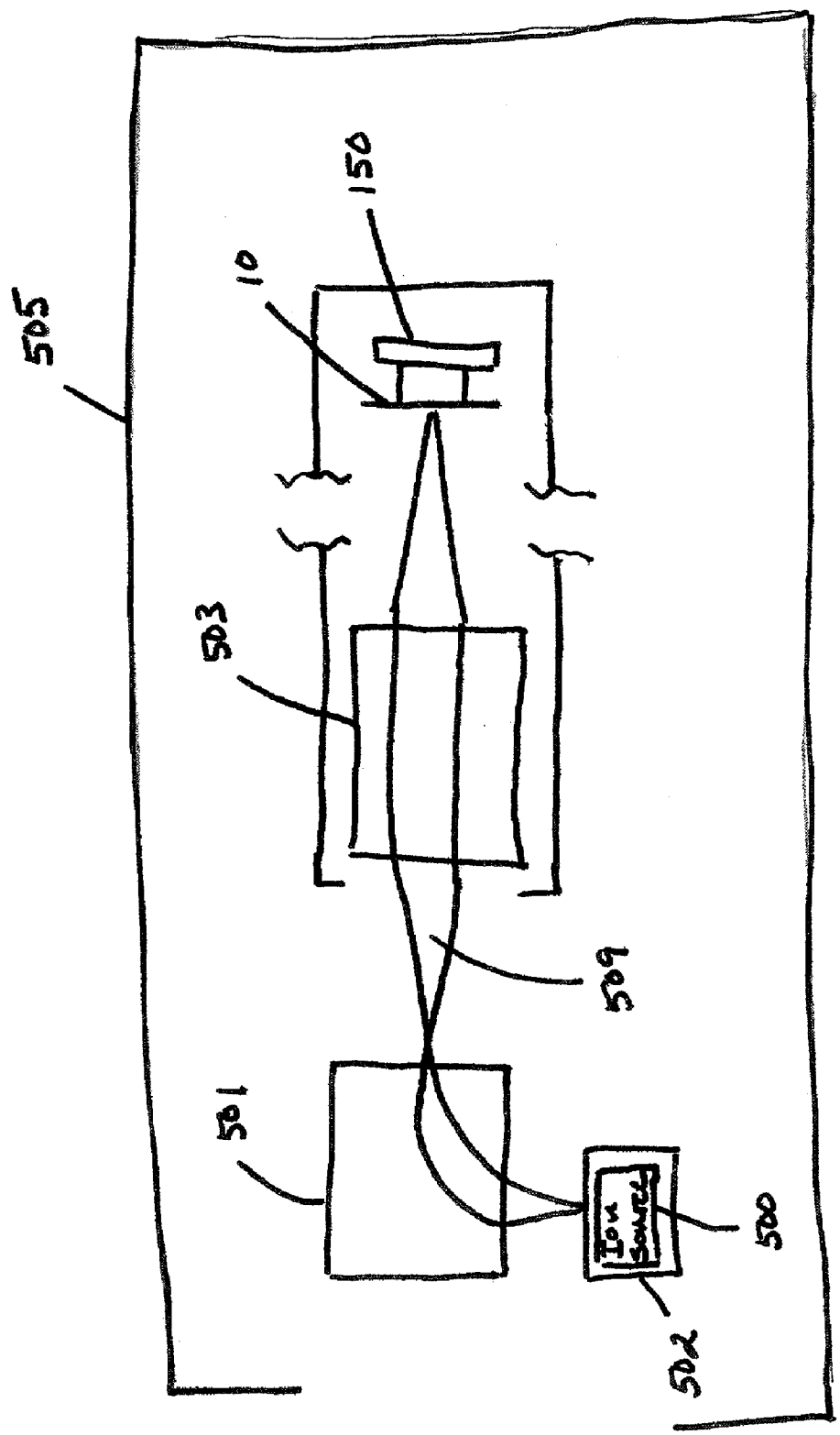
FIG. 5 is a schematic view of a monomer ion beam processing system of the present invention.

In still another embodiment of the present invention, monomer ion beam implantation is be used with the present invention when significant penetration of the drug into the surface of the medical device is desired. Because of the high energies associated with the individual atoms, implantation at increased depths may be achieved. As can be seen in FIG. 5, in a vacuum chamber 505, an ion source material 500, such as boron trifluoride for boron ions, is extracted from a plasma chamber 502 by electrostatic means, and focussed and accelerated to form an ion beam 507. A mass analysis device 501, such as a dipole sector magnet selects only the desired ion species, chosen to provide the desired chemical or physical effect upon implantation. The selected species is accelerated 503 to an energy chosen to give a very specific implant depth profile and irradiated into the surface of the stent 10 or other medical device held in place by the workpiece holder 150.

As described above for GCIB processing, one or more drugs are deposited upon a surface of the medical device and the medical device is positioned within the path of the monomer ion beam such that the surface having the drug deposited thereon will be irradiated during processing. More particularly, the workpiece holder described above is utilized due to the inherently non-planar design of the stent.

Figure 6A:
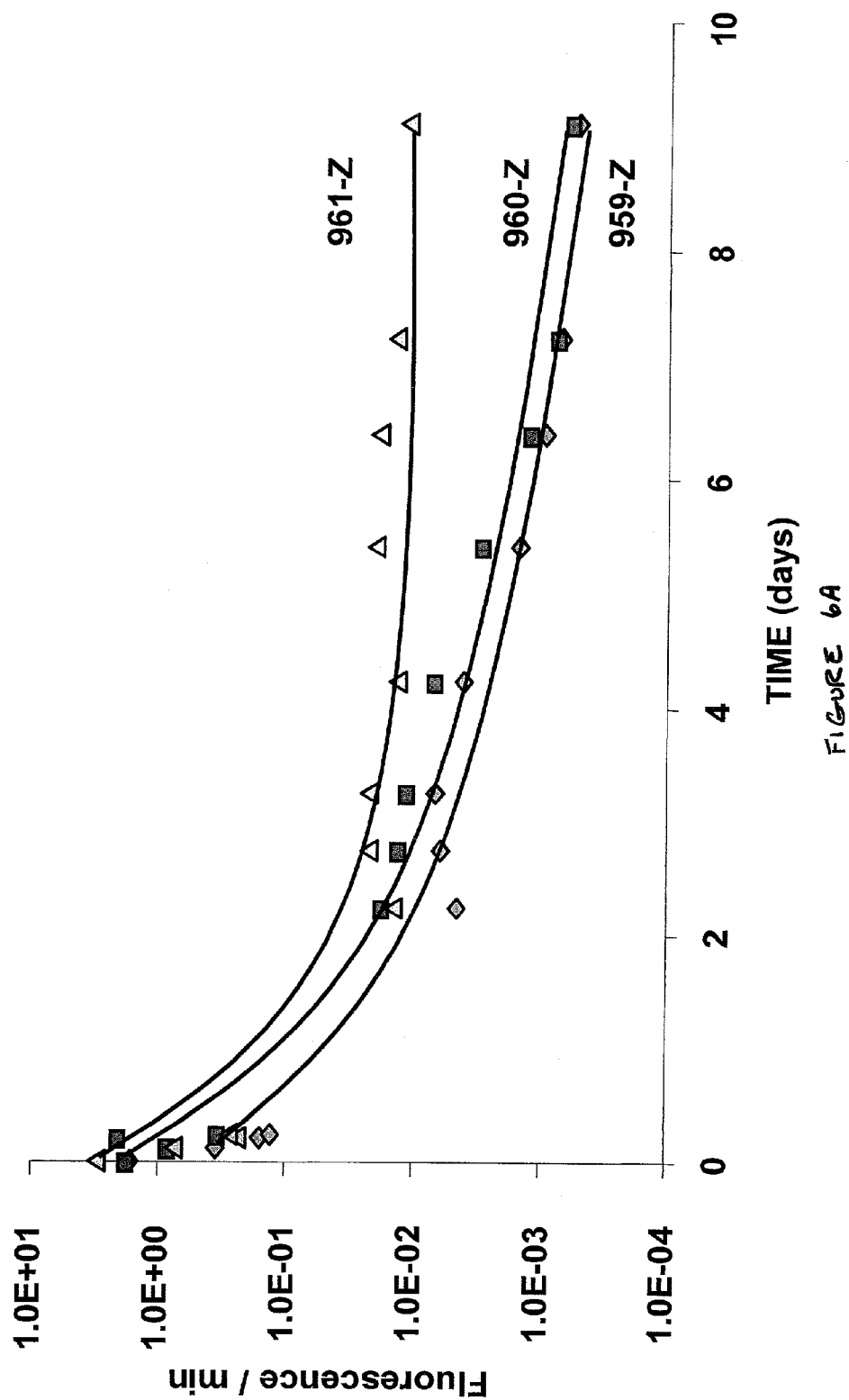
FIG. 6A is a graph showing the release rate of fluorescence over time.
Figure 6B:
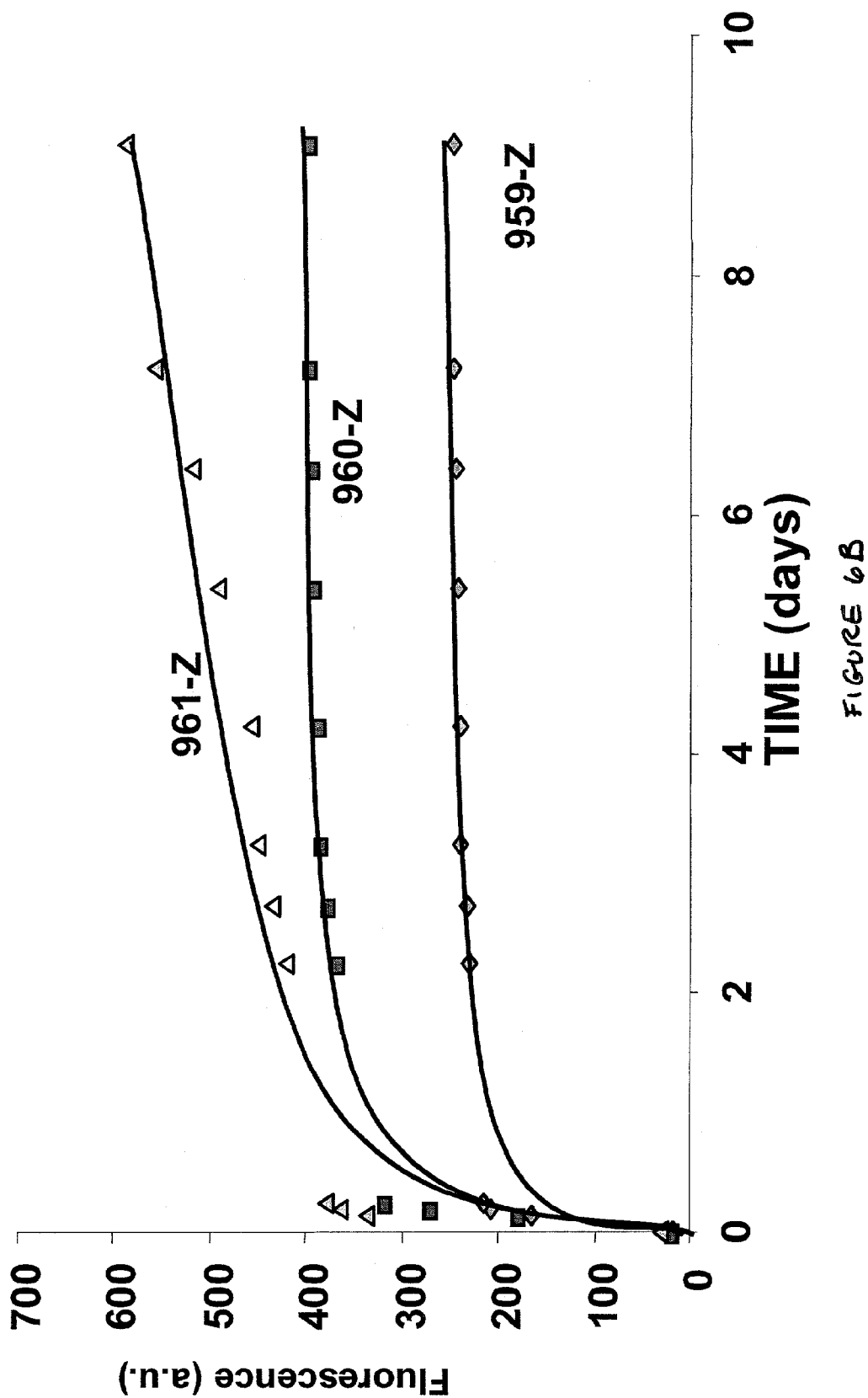
FIG. 6B is a graph showing the cumulative release rate of fluorescence over time.

Now turning to FIGS. 6A and 6B, elution rates for a substance adhered to a surface of a coronary stent using GCIB processing in accordance with the present invention is shown. To demonstrate the release rate of a molecule adhered to the surface in accordance with the present invention, the surface was irradiated and a flourescent organic dye was vapor deposited onto the freshly irradiated surface while the surface remained in the vacuum chamber. The dye elution rate was measured by observing the flourescence of the elute as a function of time. In FIG. 6A, the release rate is shown over time. In FIG. 6B, the cumulative release rate is shown over time.

Although the invention has been described with respect to various embodiments, it should be realized this invention is also capable of a wide variety of further and other embodiments within the spirit and scope of the appended claims.

What is claimed is:

1. A method for adhering a drug to a surface of a medical device comprising the steps of:
   depositing a drug onto a surface of the medical device;
   forming a gas cluster ion beam in a vacuum chamber;
   positioning the surface of the medical device in the vacuum chamber for irradiation by the gas cluster ion beam; and
   irradiating the deposited drug and the surface of the medical device with the gas cluster ion beam so as to adhere the drug to the surface of the medical device.

2. The method of claim 1, wherein the depositing step comprises depositing the drug by vapor phase deposition.

3. The method of claim 1, wherein the depositing step comprises introducing a liquid form of the drug into contact with the surface.

4. The method of claim 3, wherein:
   the liquid form is a solution of the drug in a volatile solvent; and
   the depositing step further comprises evaporating the volatile solvent.

5. The method of claim 1, wherein the drug is selected from the group consisting of anti-coagulants, antibiotics, immune-suppressing agents, vasodilators, anti-prolifics, anti-thrombotic substances, anti-platelet substances, cholesterol reducing agents and combinations thereof.

6. The method of claim 1, wherein depositing the drug comprises electrostatically coating the surface of the device with the drug in powder form.

7. The method of claim 1, wherein the irradiating step further comprises maintaining an orientation within a specific angle tolerance between the gas cluster ion beam and the surface being irradiated.

8. The method of claim 7, wherein the irradiating step further comprises scanning the gas cluster ion beam over an extended processing area of the surface.

9. The method of claim 7, wherein:
   the surface comprises an outer surface of a stent; and
   the irradiating step further comprises rotating and articulating the stent so as to permit irradiation of the outer surface of the stent.

10. A method of adhering a drug to a surface of a medical device, comprising the steps of:
    forming a first gas cluster ion beam in a vacuum chamber;
    positioning the surface of the medical device in the vacuum chamber for irradiation by the first gas cluster ion beam;
    irradiating the surface with the first gas cluster ion beam;
    depositing a drug onto the surface;
    forming a second gas cluster ion beam in the vacuum chamber; and
    irradiating the surface and the deposited drug with the second gas cluster ion beam so as to adhere the drug to the surface of the medical device.

11. The method of claim 10, wherein the medical device is a coronary stent.

12. The method of claim 10, wherein the drug is selected from the group consisting of anti-coagulants, antibiotics, immune-suppressing agents, vasodilators, anti-prolifics, anti-thrombotic substances, anti-platelet substances, cholesterol reducing agents and combinations thereof.

13. The method of claim 10, wherein at least one of the steps of irradiating with the first gas cluster ion beam and the second gas cluster ion beam further comprises maintaining an orientation within a specific angle tolerance between the first gas cluster ion beam or the second gas cluster ion beam and the surface being irradiated.

14. The method of claim 13, wherein:
    the surface comprises an outer surface of a stent; and
    at least one of the steps of irradiating with the first gas cluster ion beam and the second gas cluster ion beam further comprises rotating and articulating the stent so as to permit, irradiation of the outer surface of the stent.

15. The method of claim 13, wherein the irradiating step further comprises scanning the gas cluster ion beam over an extended processing area of the surface.

16. A method of producing a drug delivery system comprising the steps of:
    depositing a drug on a surface of a medical device; and
    irradiating the surface and the deposited drug in a vacuum chamber with a gas cluster ion beam such that a carbon matrix layer is formed during irradiation and the drug is concurrently embedded within the interstices of the carbon matrix.

* * * * *